United States Patent
Jia et al.

(10) Patent No.: US 11,154,071 B2
(45) Date of Patent: Oct. 26, 2021

(54) SWEETENER ISO-MOGROSIDE V

(71) Applicant: Glvaudan SA, Vernier (CH)

(72) Inventors: Zhonghua Jia, Cincinnati, OH (US); Xiaogen Yang, West Chester, OH (US)

(73) Assignee: Givaudan SA, Vernier (CH)

( * ) Notice: Subject to any disclaimer, the term of this patent is extended or adjusted under 35 U.S.C. 154(b) by 73 days.

(21) Appl. No.: 14/806,239

(22) Filed: Jul. 22, 2015

(65) Prior Publication Data

US 2015/0320095 A1  Nov. 12, 2015

Related U.S. Application Data

(63) Continuation of application No. 14/103,337, filed on Dec. 11, 2013, now abandoned, which is a continuation of application No. 12/672,822, filed as application No. PCT/CH2008/000336 on Aug. 7, 2008, now abandoned.

(60) Provisional application No. 60/956,436, filed on Aug. 17, 2007.

(51) Int. Cl.
   A23G 4/10 (2006.01)
   A23L 2/60 (2006.01)
   C07J 17/00 (2006.01)
   A23L 27/30 (2016.01)

(52) U.S. Cl.
   CPC ............... *A23G 4/10* (2013.01); *A23L 2/60* (2013.01); *A23L 27/33* (2016.08); *A23L 27/36* (2016.08); *C07J 17/005* (2013.01); *A23V 2002/00* (2013.01)

(58) Field of Classification Search
   CPC . A23G 4/10; A23L 27/33; A23L 27/36; A23L 2/60; C07J 17/005; A23V 2002/00
   USPC ................. 426/548, 580, 590, 615
   See application file for complete search history.

(56) References Cited

U.S. PATENT DOCUMENTS

| 4,084,010 A | 4/1978 | Takemoto et al. |
| 5,433,965 A | 7/1995 | Fischer et al. |

FOREIGN PATENT DOCUMENTS

| CN | 1683387 A | 10/2005 |
| CN | 101050230 A | 10/2007 |
| JP | 2001211854 A | 8/2001 |
| WO | 2008030121 A | 9/2007 |

OTHER PUBLICATIONS

Jia et al., A Minor, Sweet Cucurbitane Glycoside from Siraitia grosvenorii, Natural Product Communications, 2009, vol. 4, No. 6, pp. 769-772.*

Matsumoto et al., Minor Cucurbitane-Glycosides from Fruits of Siraitia Grosvenori (Cucurbitaceae), Chem. Pharm. Bull., 1990, 38(7), pp. 2030-2032.*

XP002517009, Yasushi A. Suzuki et al., Triterpene Glycosides of Siraitia Grosvenori Inhibit Rat Intestinal Maltase and Suppress the Rise in Blood Glucose Levil after a Single Oral Administration of Maltose in Rats, Journal of Agricultural and Food Chemistry, vol. 35, pp. 2941-2946, Mar. 2005.

XP002122309, Kasi Roji et al., Sweet Cucurbitane Glycosides from Fruits of Siraitia Siamensis, a Chinese Folk Medicine, Agricultural and Biological Chemistry, Japan Society for Bioscience, Biotechnology and Agrochem, vol. 53, No. 12, p. 3347, Jan. 1989.

* cited by examiner

*Primary Examiner* — Leslie A Wong
(74) *Attorney, Agent, or Firm* — Curatolo Sidoti Co., LPA; Salvatore A. Sidoti; Floyd Trillis, III

(57) ABSTRACT

Provided is the novel sweetener and sweetness enhancer iso-mogroside V, compositions comprising the sweetener/sweetness enhancer for use in consumables (food products and products place in the oral cavity including mouth wash and other dental hygiene products), and sweetened or sweetness enhanced food products comprising the novel sweetener/sweetness enhancer.

23 Claims, 2 Drawing Sheets

SWEETENER ISO-MOGROSIDE V

This application is a continuation patent application of U.S. patent application Ser. No. 14/103,337, filed Dec. 11, 2013, which in turn is a continuation of U.S. patent application Ser. No. 12/672,822, filed Mar. 16, 2010, which is a 371 application of PCT/CH2008/000336 filed Aug. 7, 2008, which claims priority to U.S. Provisional Patent Application No. 60/956,436 filed Aug. 17, 2007. The entire contents of each of the foregoing patent applications are herein incorporated by reference.

TECHNICAL FIELD

Provided is the novel high-potency sweetener and flavour enhancer iso-mogroside V, compositions comprising iso-mogroside V for use in consumables (food products or products placed in the oral cavity), sweetened consumables comprising iso-mogroside V, and sweetness enhanced consumables comprising iso-mogroside V in combination with another sweetener.

BACKGROUND

It is of interest in the food industry to find improved flavour compounds to provide more intensive high potency taste or similar taste at a higher concentration, for example, more intensive sweeteners.

Furthermore, it is of interest to enhance desired flavour sensations, for example sweet taste. By enhancing is meant the effect of a compound on a particular flavour sensation in food products or products placed in the oral cavity which is found more pronounced (stronger, enhanced) in its taste intensity and/or which is found to last longer when comparing to the product without added enhancing compound and/or which is found to have an earlier onset of the flavour sensation.

Compounds that can enhance certain flavour sensations are of great interest and may allow not only to improve/intensify the perceived flavour but also to reach a certain flavour intensity at a reduced concentration of flavour ingredients, for example less sweetener, and accordingly, less calories and/or associated undesirable flavor notes/off-notes.

Luo Han Guo is a Chinese fruit well known for its intense sweet taste. Luo Han Guo fruit is derived from *Siraitia grosvenorii* (Swingle) C. Jeffery (Curcubitaceae, formerly called *Momordica grosvenori*), a plant growing mainly in Guangxi province, China. The complete structures of the major sweet cucurbitane-type triterpenoid glycosides, named mogrosides V and IV, are known, as well as several minor sweet mogrosides including 11-oxomogroside V, siamenoside I, and neomogroside.

Applicant has discovered a previously unknown isomer of the known sweetener mogroside V, referred to herein as "iso-mogroside V", and its high sweetening properties when compared to its known isomer.

Furthermore, preliminary experiments indicate that iso-mogroside V has a particularly high flavour enhancing effect on sweeteners when compared to its known isomer.

By using iso-mogroside V in combination with one or more flavour compound, in particular sweeteners, compositions and consumables (food products, products placed in the oral cavity) can be formed which have an enhanced effect of the associated flavour sensation, in particular an enhanced sweetness.

The chemical structure of iso-mogroside V, systematic name 3-[(4-O-β-D-glucopyranosyl-β-D-glucopyranosyl)oxy]-mogrol-24-O-β-D-glucopyranosyl-(1→2)-O-[β-D-glucopyranosyl-(1→6)]-β-D-glucopyranoside, is shown below.

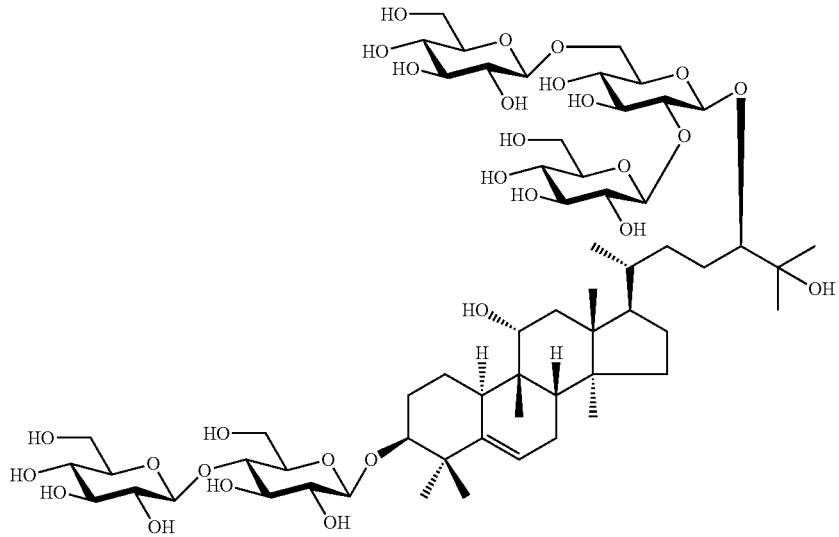

By using iso-mogroside V compositions, consumables can be formed which have an improved and/or enhanced sweetness.
The chemical structures of iso-mogroside V and mogroside V are shown in comparison below.
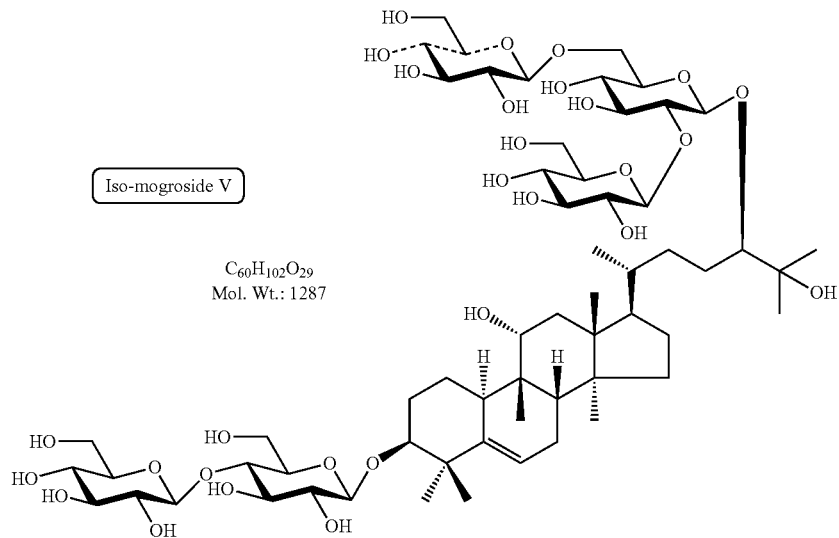
Iso-mogroside V
$C_{60}H_{102}O_{29}$
Mol. Wt.: 1287
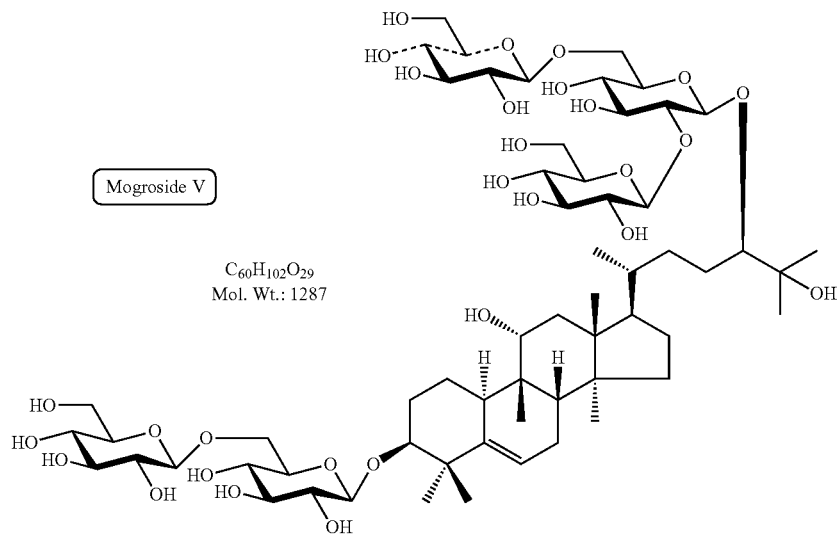
Mogroside V
$C_{60}H_{102}O_{29}$
Mol. Wt.: 1287

The newly identified isomer is believed to be a native component of swingle fruit, as it was found in a number of commercial swingle extracts from various sources that had been subjected to various harvesting and extracting methods, but all contained low amounts of the isomer.

SUMMARY

Provided are the following:
(1) The compound of formula I below.

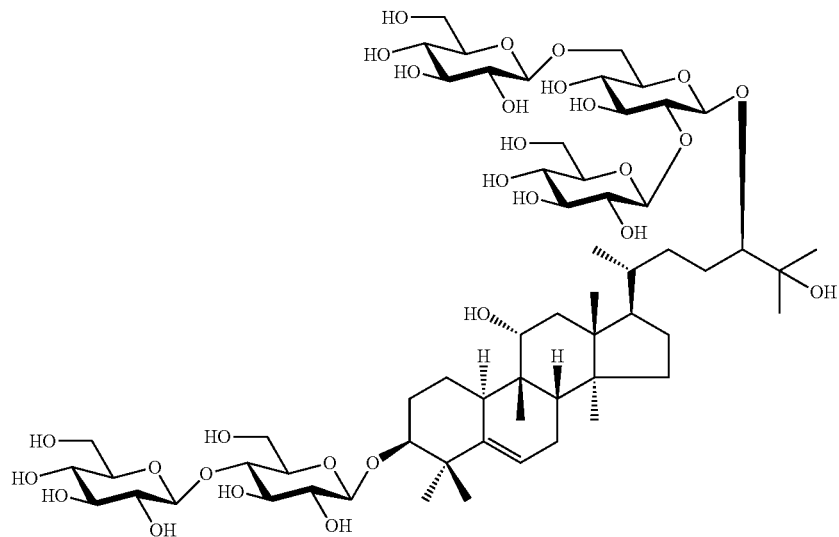

(2) A composition comprising isolated or purified iso-mogroside V.

(3) A composition enriched in iso-mogroside V to a total concentration of iso-mogroside V of at least 10% (wt/wt).

(4) The composition of item (3) enriched by chemical purification.

(5) The composition of any one of items (2) to (4) and at least one excipient.

(6) The composition of any one of items (2) to (5) which is a consumable.

(7) The composition of any one of items (4) to (6) wherein iso-mogroside V is present in a concentration from 0.2 ppm to 800 ppm or more.

(8) The composition of any one of items (4) to (7) comprising one or more additional flavour ingredients, wherein the concentration of isomogroside V is sufficient to cause an enhancement of the flavour, and wherein the concentration of the flavour is sufficiently high to be above the detection threshold for the flavour sensation when combined with isomogroside V.

(9) The composition of item (8), wherein the flavour ingredient is a sweetener.

(10) The composition of item (9) wherein the one or more sweetener is selected from the group consisting of sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, mogroside IV, siamenoside I, mogroside V, trilobatin.

(11) The composition of any one of items (4) to (10) wherein the consumable is a water-based consumable and iso-mogroside V is present in a concentration from 0.2 ppm to 300 ppm or more, and wherein the water-based consumable includes but is not limited to beverage, water, aqueous beverage, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacoa (water-based), tea-based drink, coffee-based drinks, cacao-based drink, syrup, frozen fruit, frozen fruit juice, water-based ice, fruit ice, sorbet, dressing, salad dressing, sauce, soup, and beverage botanical materials (whole or ground), or instant powder for reconstitution (coffee beans, ground coffee, instant coffee, cacao beans, cacao powder, instant cacao, tea leaves, instant tea powder).

(12) The composition of any one of items (4) to (10) wherein the consumable is a solid dry consumable and iso-mogroside V is present in a concentration from 0.2 ppm to 300 ppm or more, and the solid dry consumable includes but is not limited to cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, botanical materials (whole or ground), and instant powders for reconstitution.

(13) The composition of any one of items (4) to (10) wherein the consumable is selected from the group of a dairy product, dairy-derived product and dairy-alternative product, and iso-mogroside V is present in a concentration from 0.3 ppm to 500 ppm or more, and wherein the consumable includes but is not limited to milk, fluid milk, cultured milk product, cultured and noncultured dairy-based drink, cultured milk product cultured with *lactobacillus*, yoghurt, yoghurt-based beverage, smoothy, lassi, milk shake, acidified milk, acidified milk beverage, butter milk, kefir, milk-based beverages, milk/juice blend, fermented milk beverage, icecream, dessert, sour cream, dip, salad dressing, cottage cheese, frozen yoghurt, soy milk, rice milk, soy drink, and rice milk drink.

(14) A method of providing a sweetened consumable by admixing isolated or purified iso-mogroside V or the composition of any one of items (2) to (13) to a consumable.

(15) A method of providing a sweetened consumable by admixing iso-mogroside V or the composition of any one of items (2) to (13) to a consumable wherein the resulting iso-mogroside concentration in the consumable is enriched compared to the natural iso-mogroside concentration.

(16) A method of enhancing the taste sensations associated with flavour ingredients, wherein isolated or purified iso-mogroside V and one or more flavour ingredient are admixed to provide a flavour-enhanced composition or consumable.

(17) A method of enhancing the taste sensations associated with flavour ingredients by admixing iso-mogroside V or the composition of any one of items (2) to (13) to a consumable, wherein the resulting iso-mogroside concentration in the consumable is enriched compared to the natural iso-mogroside concentration.

(18) The method of any one of items (14) to (17), wherein iso-mogroside V is added to a total concentration from 0.2 ppm to 500 ppm, or more.

19. The method of any one of items (14) to (18) wherein the flavour ingredient is a sweetener.

(20) The method of item (19) wherein the sweetener is selected from the group as defined under item (10).

(21) The method of any one of items (14) to (20) wherein the consumable is a water-based consumable as defined under item (11) and iso-mogroside V is present in a concentration from 0.2 ppm to 300 ppm or more.

(22) The method of any one of items (14) to (20) wherein the consumable is a solid dry consumable as defined under item (12) and iso-mogroside V is present in a concentration from 0.2 ppm to 300 ppm or more.

(23) The method of any one of items (14) to (20) wherein the consumable is selected from the group of a dairy product, dairy-derived product and dairy-alternative product as defined under item (13) and iso-mogroside V is present in a concentration from 0.3 ppm to 500 ppm or more.

DETAILED DESCRIPTION

Flavour compositions comprise iso-mogroside V and optionally at least one food grade excipient. Suitable excipients for flavour compositions are well known in the art and include, for example, without limitation, solvents (including water, alcohol, ethanol, oils, fats, vegetable oil, and miglyol), binders, diluents, disintegranting agents, lubricants, flavoring agents, coloring agents, preservatives, antioxidants, emulsifiers, stabilisers, flavor-enhancers, sweetening agents, anti-caking agents, and the like. Examples of such carriers or diluents for flavours may be found e.g. in "Perfume and Flavor Materials of Natural Origin", S. Arctander, Ed., Elizabeth, N.J., 1960; in "Perfume and Flavor Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

The flavour composition may contain additional flavour ingredients including flavour compounds, flavours from natural sources including botanical sources and including ingredients made by fermentation.

The flavour composition may have any suitable form, for example liquid or solid, wet or dried, or in encapsulated form bound to or coated onto carriers/particles or as a powder.

Iso-mogroside V and its flavour compositions described herein can be added to consumables (food products and any products placed within the oral cavity) to provide a sweet taste. Consumables include, without limitation, food, beverages, nutraceuticals and dental care products including mouth wash and dental hygiene articles, and solid flavoured products such as dental floss, drinking straws and other plastic products where flavour can be added to the formulation or that can be coated.

Consumables include all food products, including but not limited to, cereal products, rice products. tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

Iso-mogroside V can be used in various consumables including but not limited to water-based consumables, solid dry consumables and dairy products, dairy-derived products and dairy-alternative products.

Water-based consumables include but are not limited to beverage, water, aqueous drink, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacoa (water-based), tea-based drink, coffee-based drink, cacao-based drink, syrup, frozen fruit, frozen fruit juice, water-based ice, fruit ice, sorbet, dressing, salad dressing, sauce, soup, and beverage botanical materials (whole or ground), or instant powder for reconstitution (coffee beans, ground coffee, instant coffee, cacao beans, cacao powder, instant cacao, tea leaves, instant tea powder).

Solid dry consumables include but are not limited to cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, and botanical materials (whole or ground), and instant powders for reconstitution as mentioned above.

For water-based or solid dry consumables a useful concentration may be from 0.2 to 300 ppm or more.

In certain products a higher sweetener concentration is usually necessary to reach a similar sweetness intensity, for example in dairy products, dairy-derived products and dairy-alternative products. Dairy-derived food products contain milk or milk protein. Dairy-alternative products contain (instead of dairy protein derived from the milk of mammals) protein from botanical sources (soy, rice, and other protein-rich plant materials).

Dairy products, dairy-derived products and dairy-alternative products include but are not limited to milk, fluid milk, cultured milk product, cultured and noncultured dairy-based drinks, cultured milk product cultured with *lactobacillus*, yoghurt, yoghurt-based beverage, smoothy, lassi, milk shake, acidified milk, acidified milk beverage, butter milk, kefir, milk-based beverage, milk/juice blend, fermented milk beverage, icecream, dessert, sour cream, dip, salad dressings, cottage cheese, frozen yoghurt, soy milk, rice milk, soy drink, rice milk drink.

Milk includes, but is not limited to, whole milk, skim milk, condensed milk, evaporated milk, reduced fat milk, low fat milk, nonfat milk, and milk solids (which may be fat or nonfat).

For dairy products, dairy-derived products and dairy-alternative products, a useful concentration will be from about 0.3 to 500 ppm or higher, and may be up to 550 ppm, 600 ppm, 650 ppm, 700 ppm, or 750 ppm.

For a sufficient sweetening effect on its own, iso-mogroside V should usually have a concentrations of at least 10 ppm, for dairy, dairy-derived and dairy-alternative products at least 15 ppm. Depending on the degree of sweetness to be achieved, its concentration will usually be much higher in most applications (from 50 ppm or 100 ppm or higher).

For flavor enhancement in combination with a sweetener, the appropriate concentration of the flavour enhancer/(iso-mogroside V) can be easily tested by an organoleptic titration. This technique is well known in the field of sensory analysis. An appropriate concentration is from near the sweetness detection threshold of iso-mogroside V, about 0.2 ppm in water (equivalent sweetness intensity to about 0.5% sucrose, which is very slightly sweet), to about 20 ppm, 30 ppm, 50 ppm, 100 ppm, 200 ppm, 300 ppm, 400 ppm, 500 ppm, or higher.

The sweeteners include, but are not limited to, the sugars sucrose, fructose, glucose, high fructose corn syrup (containing fructose and glucose), xylose, arabinose, and rhamnose, the sugar alcohols erythritol, xylitol, mannitol, sorbitol, and inositol, and the artificial sweeteners AceK, aspartame, neotame, sucralose, saccharine, naringin dihydrochalcone (NarDHC), neohesperidin dihydrochalcone (NDHC), rubusoside, rebaudioside A, stevioside, mogroside IV, siamenoside I, mogroside V, trilobatin, and combinations of these sweeteners.

When used as sweeteners, these compounds will usually be used in concentrations isosweet to about 2% sucrose or higher.

Sucrose, also known as table sugar or saccharose, is a disaccharide of glucose and fructose. Its systematic name is α-D-glucopyranosyl-(1→2)-β-D-fructofuranose. Fructose and glucose are monosaccharide sugars.

High fructose corn syrup (HFCS) consists of a mixture of glucose and fructose. Like ordinary corn syrup, the high fructose variety is made from corn starch using enzymes. The fructose content of corn syrup (glucose) is increased through enzymatic processing. Common commercial grades of high fructose corn syrup include fructose contents of 42%, 55%, or 90%. The 55% grade is most commonly used in soft drinks.

Erythritol (systematic name 1,2,3,4-butanetetrol) is a natural non-caloric sugar alcohol.

AceK, aspartame, neotame and and sucralose are artificial sweeteners.

Acesulfam potassium (AceK) is the potassium salt of 6-methyl-1,2,3-oxathiazine-4(3H)-one 2,2-dioxide, an N-sulfonylamide. It is also known as Acesulfam K or AceK, or under various trademark names including Sunett® and Sweet One®. In the European Union it is also known under the E number (additive code) E950.

Aspartame is the name for aspartyl-phenylalanine-1-methyl ester, a dipeptide. It is known under various trademark names including Equal®, and Canderel®. In the European Union, it is also known under the E number (additive code) E951.

Sucralose is the name for 6-dichloro-1,6-dideoxy-β-D-fructo-furanosyl 4-chloro-4-deoxy-α-D-galactopyranoside, which is a chlorodeoxysugar. It is also known by the trade name Splenda®. In the European Union, it is also known under the E number (additive code) E955.

Naringin dihydrochalcone (NarDHC) is also known as -[4-[[2-O-(6-Deoxy-L-mannopyranosyl)-D-glucopyranosyl]oxy]-2,6-dihydroxyphenyl]-3-(4-hydroxyphenyl)-1-propanone. The chemical structure is given below.

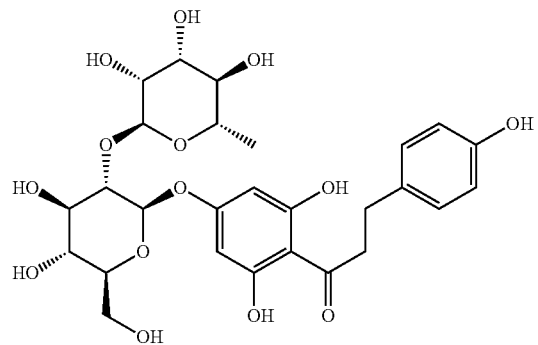 [SMILES: C[C@@H]1O[C@@H](O[C@@H]2[C@@H](Oc3cc(O)c(C(=O)CCc4ccc(O)cc4)c(O)c3)O[C@@H](CO)[C@H](O)[C@H]2O)[C@H](O)[C@H](O)[C@H]1O]

*Rubus* extract is the extract of the plant *Rubus suavissimus* and contains rubusoside. Rubusoside may be purified from the extract and used in purified form or the extract may be used. Alternatively to *Rubus suavissimus* extract, another botanical extract containing a sufficient amount of rubusoside may be used. The chemical structure of rubusoside is given below.

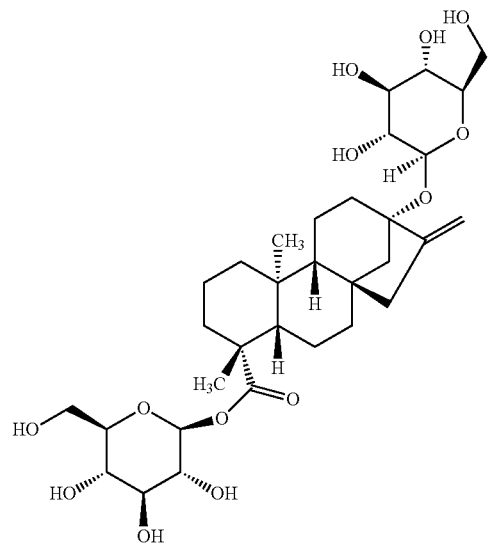

Stevioside is a terpenoid glycoside also known as *stevia*, and is found in extracts of the plant *Stevia rebaudiana*.

Rebaudioside A is a terpenoid glycoside that is found in extract of *Stevia rebaudiana*. The chemical structure is given below.

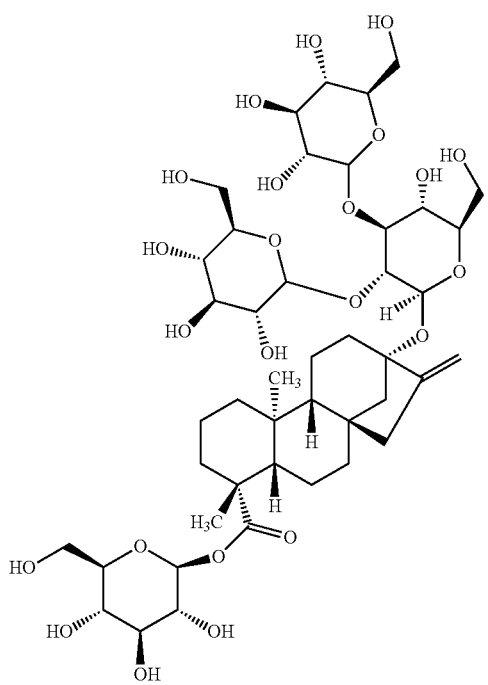

Trilobatin or 1-[4-(β-D-glucopyranosyloxy)-2,6-dihydroxyphenyl]-3-(4-hydroxyphenyl)-1-propanone is also known as p-Phlorizin, Phloretin 4'-glucoside, Phloretine-4'-glucoside, Prunin dihydrochalcone, or p-Phloridzin. It is a natural dihydrochalcone type sweetener that occurs in the Chinese sweet tea plant *Lithocarpus polystachyus*, in the apple species *Malus trilobata*, and their extracts. Its chemical structure is given below.

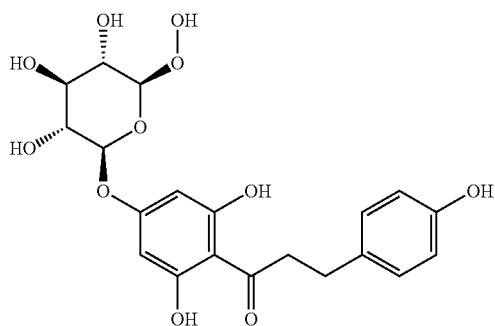 [SMILES: O=C(CCc1ccc(O)cc1)c1c(O)cc(O[C@@H]2O[C@H](OO)[C@@H](O)[C@H](O)[C@H]2O)cc1O]

The sweeteners or iso-mogroside V may be used in pure or partly purified, isolated or natural form; they may be chemically synthesised, produced by biotechnological processes including fermentation, or isolated from a natural source, in particular a botanical source (including, without limitation, fruits, swingle fruit, sugar cane, sugar beet), for example a plant extract (for example, without limitation, *rubus* extract for rubusoside and swingle extract for mogrosides and siamenoside I) or syrup including, without limitation, corn syrup, high fructose corn syrup, honey, molasses, maple syrup, fruit concentrates, and other syrups and extracts.

Optionally, one or more additional sweetness enhancers may be used in combination with isolated/purified/synthesised iso-mogroside V or compositions enriched in iso-mogroside V. These optional sweetness enhancers include but are not limited to naringin dihydrochalcone (NarDHC), mogroside V, swingle extract, rubusoside, *rubus* extract, stevioside, and rebaudioside A, and neohesperidin dihydrochalcone (NDHC).

The additional sweetness enhancers can be used at or near their detection threshold concentration; for naringin dihydrochalcone this concentration is from 2 to 60 ppm, for rubusoside from 1.4 ppm to 56 ppm, for *rubus* extract from 2 ppm to 80 ppm, for mogroside V from 0.4 ppm to 12.5 ppm, for swingle extract from 2 to 60 ppm, for stevioside from 2 to 60 ppm, for rebaudioside A from 1 to 30 ppm, and for neohesperidin dihydrochalcone from 1 to 5 ppm. They can also be used at a higher concentration, depending on the mixture, individual concentrations of sweeteners and sweetness enhancers, associated calories and off-notes.

EXAMPLES

All percentages given are wt/wt, unless indicated otherwise.

The Luo Han Guo or swingle extract that was employed had a total mogrosides content of about 80%, a mogroside V content of about 25-30%, and is commercially available from Fuzhou Corona Science & Technology Co., Ltd., Fuzhou, P. R. China.

General Experimental Procedures for the Purification and Structural Analysis of the Compounds in Examples 3 and 4:

Optical rotations were measured with a Rudolph Autopol IV polarimeter (Rudolph Research Analytical, Hackettstown, N.J., USA).

Nuclear magnetic resonance (NMR) spectra were recorded on a Bruker DRX avance 500 spectrometer (Bruker BioSpin, Billerica, Mass.). Chemical shifts are given in δ (ppm) referring to the residual solvent peak.

Preliminary purification was carried out on Diaion HP-20 (Mitsubishi Chemical, Tokyo, Japan) resin.

Low pressure chromatography was performed on a Biotage Flash system using a C-18 cartridge (40+M, 35-70 μm).

High performance liquid chromatography (HPLC) was performed on an Agilent 1100 analytical and preparative HPLC systems (Agilent Technologies, Santa Clara, Calif.) with a Phenomenex Lunar C18(2) column, 5 μm, 4.6×150 mm for analytical scale and 21.2×250 mm for preparative scale) (Phenomenex, Torrance, Calif.). Liquid chromatography-mass spectrometry (LC-MS) was performed using a Waters Q-Tof micro mass spectrometer coupled with a Waters 2795 separation module (Waters, Milford, Mass.).

Structural identification (NMR and MS) methods employed included Correlated Spectroscopy (COSY), Totally Correlated Spectroscopy (TOCSY), Nuclear Overhauser Effect Spectroscopy (NOESY), Heteronuclear Single Quantum Coherence (HSQC), Heteronuclear Multiple Bond Coherence (HMBC), Distortionless Enhancement by Polarization Transfer (DEPT), negative electrospray ionization time-of-flight mass spectrometry (ESI-TOF MS), High resolution electrospray ionization time-of-flight mass spectrometry (HRESI-TOFMS), electrospray ionization tandem mass spectrometry (ESI-MS/MS).

All of these methods are standard methods and it is well known to the skilled person how to carry them out.

Example 1a

Figure 1:
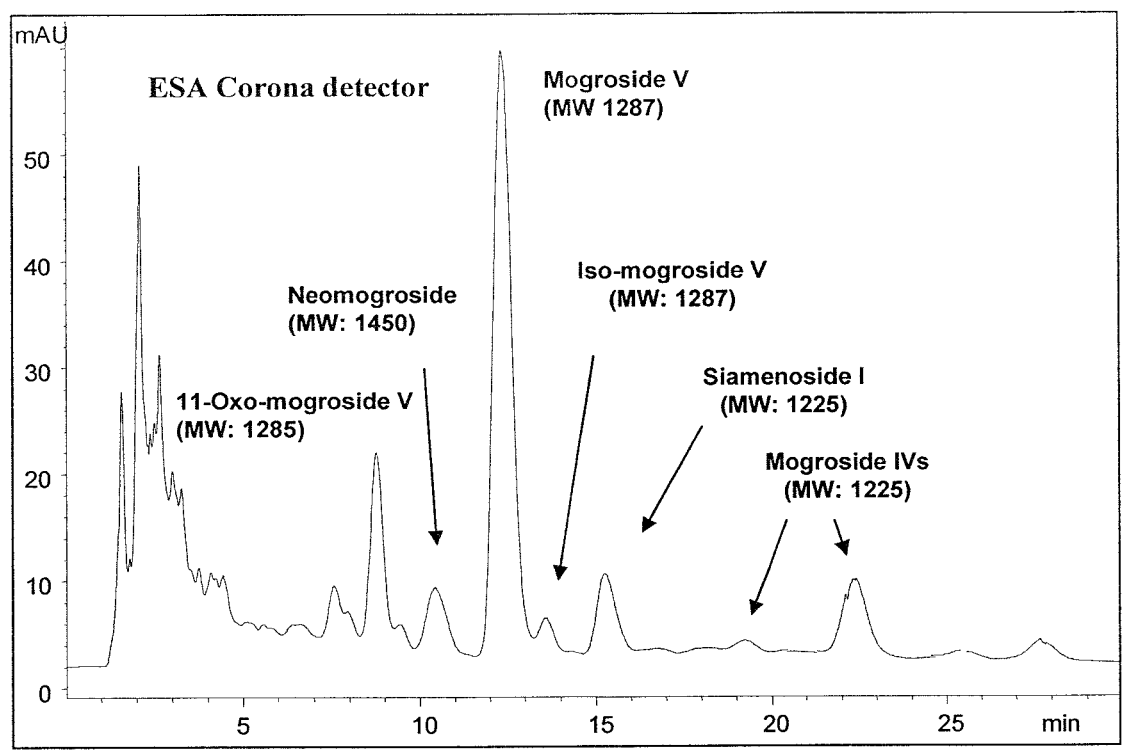
FIG. 1 is an HPLC profile and peak identity graph of the swindle extract described in Example 3.

Comparison of the Sweetness of Mogroside V and Iso-Mogroside V

The intensity of sweet taste of iso-mogroside V when compared to mogroside V was determined in water using near-sweetness detection threshold concentrations. The direct comparison was carried out by a panel of 4 sweet sensitive panelists. Blind samples (identity unidentifiable by panelists) were randomly presented to panelists in 15 ml aliquots at ambient temperature. Sensory evaluation started with the lower sample concentration (10 ppm).

The results are indicated in the table below.

| sample concentrations [ppm] | Taste of iso-mogroside V samples compared to mogroside V |
| --- | --- |
| 10 | sweeter |
| 20 | sweeter |

At 10 ppm, two panelists indicated iso-mogroside V is sweeter than mogroside V. At 20 ppm level, all 4 panelists indicated iso-mogroside V is sweeter than mogroside V.

Example 1b

Comparison of the Sweetness Enhancement of Iso-Mogroside V at Near Threshold Concentration The sweetness enhancement properties of iso-mogroside V was determined using a sample having a concentration of 10 ppm iso-mogroside V, which is near the sweetness detection threshold, in 7% sucrose solution.

The iso-mogroside V sample was directly compared to samples of 7%, 8% or 9% sucrose, and panelists were instructed to compare the sweetness intensity of the samples.

The comparisons were carried out by a panel of 6 sweet sensitive panelists. All samples were presented to panelists in 15 ml aliquots at ambient temperature. Panelists compared the iso-mogroside V sample to each of the sucrose samples. The results are indicated below.

Iso-mogroside V samples showed a sweetness at least equal to 8% sucrose. The majority of panelists (5 of 6) found that the sample was as sweet or sweeter as 8% sucrose, and 1 of 6 panelist found the iso-mogroside sample to be sweeter than 7% but less sweet than 8% sucrose.

The sweetness threshold of iso-mogroside V in water was determined to be 10 ppm, isosweet to 0.5% sucrose (see example 2), therefore an enhancement effect of at least equal to 0.5% sucrose or higher was determined.

Example 2

Determination of the Sweetness Threshold of Iso-Mogroside V

Iso-mogroside V was evaluated by 5 sweet sensitive panelists at 10 ppm in water for isointensity to sucrose solutions (0.5, 1.0 and 1.5% sucrose) using a paired comparison method. Samples were paired and tasted left to right with rinsing of the mouth (water) in-between. 20 ppm iso-mogroside V was evaluated as described but with 4 sweet sensitive panelists and 0.5, 1.0 and 1.5% sucrose. The results are indicated in the table below.

| Iso-mogroside V [ppm] | Taste of iso-mogroside V samples compared to sucrose | Sucrose [% wt/wt] |
| --- | --- | --- |
| 10 | sweeter | 0 |
| 10 | isosweet | 0.5 |
| 10 | less sweet | 1.0 |
| 20 | sweeter | 0.5 |
| 20 | isosweet | 1% |
| 20 | less sweet | 1.5% |

10 ppm iso-mogroside V was sweeter than water (0% sucrose), less sweet than 1% sucrose, and isosweet to 0.5% sucrose (barely sweet). The sweetness detection threshold concentration of iso-mogroside V in water is accordingly about 10 ppm. The 20 ppm of iso-mogroside V sample was sweeter than 0.5% sucrose and less sweet than 1.5% sugar, but was found to be isosweet to 1% sucrose.

At the low concentration of 10 ppm iso-mogroside V is isosweet to 0.5% sucrose, showing its high potency sweetener characteristic equaling about 500 times the sweetness of sucrose.

Example 3

LC-MS Analysis of Swingle Extract

The analysed sample was swingle extract. Sample was dissolved in MeOH at a concentration of 1% and filtered. LC-MS analysis was performed using a Waters Q-Tof micro mass spectrometer coupled with a Waters 2795 separation module. The HPLC conditions were as follows: Phenomenex Luna C18(2), 5 µm, 4.6×150 mm, 55% MeOH—H$_2$O 30 min, 0.8 ml/min; analogue detector: ESA Corona and UV 210 nm.

The HPLC profile and peak identities are shown in FIG. 1.

LC-MS analysis of the swingle extract identified the major sweet mogroside (mogroside V) along with a few known minor analogues (11-oxo-mogroside V, siamenoside I, mogrosides IVa, and IVe). Further LC-MS analysis of the minor components indicated the presence of a previously unreported component which had nearly the same HPLC retention time and exactly the same molecular composition as the major sweet compound, mogroside V.

Example 4

Purification of Iso-Mogroside V

Swingle extract (20 g) was applied to a column of Diaion HP-20 (600 g) (Mitsubishi Chemicals, Tokyo, Japan) and washed successively with 30, 50, 70% MeOH/water and 100% methanol, using 3000 ml for each washing step. Part of the 70% methanol fraction (2.23 g) was purified over a reversed phase C-18 column using a Biotage Flash chromatography.

Further preparative HPLC purification (4 repetitions) of the fractions of interest employing a Phenomenex preparative column (Luna C18(2), 5 µm, 21.2×250 mm) afforded iso-mogroside V (8.0 mg) in a purity of about 95 to 98%.

Example 5

Structural Identification of Iso-Mogroside V

Iso-mogroside V (1) was isolated as an amorphous solid with an $[\alpha]^{20}_D$ −2.1 (c 0.57, MeOH) and a molecular formula of $C_{60}H_{102}O_{29}$ determined from its positive ion high resolution ESI-TOF MS (at m/z 1287.6530 [M+H]$^+$).

The aglycone part of iso-mogroside V (structural formula shown below) was identified as mogrol by analysis of 1D ($^1$H, $^{13}$C and DEPT), and 2D (COSY, TOCSY, HSQC and NOESY) NMR and further confirmed by the long-range connectivity observed in HMBC, the results of which are listed in the table below.

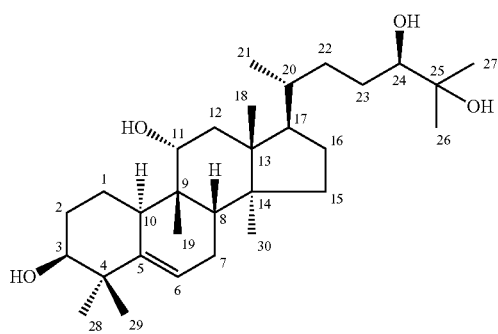

TABLE

Aglycones of iso-mogroside V (1) and mogroside V (2) in CD$_3$OD: $^1$H and $^{13}$C NMR data.

| number of carbon atom as shown in the structural formula above | $^{13}$C | $^1$H |
| --- | --- | --- |
| 1 | 27.4 | 1.49, 2.23 dd (2.85, 12.4) |
| 2 | 29.8 | 1.93 (2H) |
| 3 | 88.3 | 3.47 m |
| 4 | 43.0 | — |
| 5 | 145.2 | — |
| 6 | 119.8 | 5.49 d (6.0) |
| 7 | 25.3 | 1.81 dd (5.0, 12.5), 2.39 dd (6.8, 12.5) |
| 8 | 44.8 | 1.67 d (7.6) |
| 9 | 41.0 | — |
| 10 | 37.4 | 2.50 d (12.3) |
| 11 | 79.5 | 3.86 |
| 12 | 41.2 | 1.82, 1.88 |
| 13 | 48.4 | — |
| 14 | 50.7 | — |
| 15 | 35.5 | 1.14, 1.21 |
| 16 | 29.6 | 1.33, 1.98 |
| 17 | 51.9 | 1.63 d (9.2) |
| 18 | 17.3 | 0.89 s |
| 19 | 26.3 | 1.11 s |
| 20 | 37.6 | 1.46 m |
| 21 | 19.5 | 0.98 d (6.3) |
| 22 | 34.2 | 1.49, 1.56 |
| 23 | 30.1 | 1.85 |
| 24 | 93.5 | 3.40 |
| 25 | 70.4 | — |
| 26 | 26.5 | 1.12 s |
| 27 | 24.0 | 1.15 s |
| 28 | 28.1 | 1.08 s |
| 29 | 26.4 | 1.19 s |
| 30 | 20.2 | 0.89 s |

For the sugar parts of iso-mogroside V (1), the $^1$H and $^{13}$C NMR displayed five anomeric protons at [δ 4.77 d (J=7.2 Hz), 4.43 d (J=7.4 Hz), 4.42 (J=8.0 Hz), 4.31 (J=8.0 Hz), 4.29 (J=7.7 Hz) and carbons at (δ 106.3, 104.6, 104.5, 104.4, 104.2) (see figure and table below).

The sequence of the oligosaccharide chains were established by a combination of COSY, TOCSY, HSQC, HMBC and NOESY. To facilitate the proton assignments, the five anomeric protons were consecutively labeled by the letters G-1 to G-5 from the lower field (see figure which shows iso-mogroside V and the results in the table below).

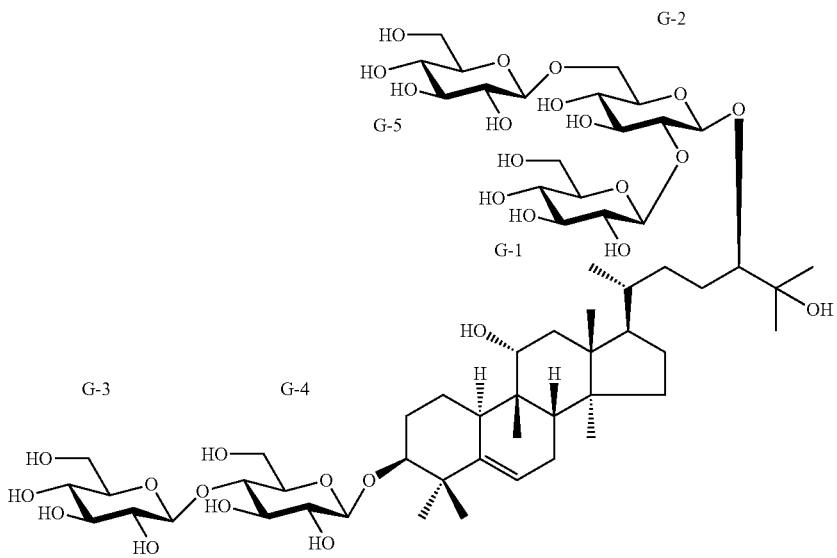

TABLE

Sugar parts of iso-mogroside V (1) and mogroside V (2) in CD$_3$OD: $^1$H and $^{13}$C NMR Data

| identities (G-1 to G5) of the sugar carbon atoms as indicated in the structural formula above, using conventional numbering | Iso-mogroside (1) | | Mogroside (2) | |
|---|---|---|---|---|
| | $^{13}$C | $^1$H | $^{13}$C | $^1$H |
| G-1 | | | | |
| 1 | 104.5 | 4.77 d (7.2) | 104.6 | 4.78 d (7.7) |
| 2 | 75.7 | 3.28 | 75.8 | 3.28 |
| 3 | 78.0 | 3.36 | 78.0 | 3.37 |
| 4 | 72.5 | 3.22 | 72.5 | 3.23 |
| 5 | 78.1 | 3.28 | 78.2 | 3.28 |
| 6 | 63.7 | 3.86 | 63.7 | 3.87 |
| | | 3.65 | | 3.65 |
| G-2 | | | | |
| 1 | 104.2 | 4.43 d (7.4) | 104.3 | 4.44 d (7.2) |
| 2 | 81.3 | 3.61 | 81.2 | 3.62 |
| 3 | 78.5 | 3.59 | 78.4 | 3.58 |
| 4 | 71.6 | 3.34 | 71.4 | 3.34 |
| 5 | 76.5 | 3.51 | 76.3 | 3.51 |
| 6 | 70.2 | 3.63 | 70.0 | 3.64 |
| | | 4.24 br.d (8.7) | | 4.24 br.d (8.7) |
| G-3 | | | | |
| 1 | 104.6 | 4.42 d (8.0) | 104.9 | 4.43 d (7.8) |
| 2 | 75.8 | 3.21 | 75.7 | 3.20 |
| 3 | 77.8 | 3.36 | 77.7 | 3.36 |
| 4 | 71.5 | 3.27 | 71.5 | 3.28 |
| 5 | 78.2 | 3.29 | 78.1 | 3.25 |
| 6 | 62.6 | 3.86 | 62.8 | 3.86 |
| | | 3.65 | | 3.67 |
| G-4 | | | | |
| 1 | 106.3 | 4.31 d (8.0) | 106.5 | 4.29 d (7.7) |
| 2 | 75.5 | 3.26 | 75.3 | 3.21 |
| 3 | 76.6 | 3.48 | 78.8 | 3.37 |
| 4 | 80.9 | 3.55 | 71.7 | 3.28 |
| 5 | 77.8 | 3.36 | 77.4 | 3.41 |
| 6 | 62.1 | 3.83 (2H) | 69.9 | 3.81 dd (12.0, 5.6) |
| | | | | 4.06 dd (12.0, 1.7) |
| G-5 | | | | |
| 1 | 104.4 | 4.29 d (7.7) | 104.5 | 4.28 d (7.7) |
| 2 | 75.3 | 3.21 | 75.3 | 3.21 |
| 3 | 78.2 | 3.36 | 78.2 | 3.36 |
| 4 | 71.6 | 3.29 | 71.7 | 3.29 |
| 5 | 78.3 | 3.27 | 78.2 | 3.26 |
| 6 | 62.8 | 3.85 | 62.8 | 3.86 |
| | | 3.66 | | 3.67 |

Starting from the anomeric protons of each sugar unit, all the hydrogens within each spin system were traced using COSY with the aid of TOCSY and NOESY. The individual spin-systems of each sugar can be discerned from the sub-spectra corresponding to the anomeric protons in the TOCSY (mixing time=120 ms). A NOESY experiment (mixing time=600 ms) in addition to the Nuclear Overhauser Effect (NOE) contacts across the glycosidic bonds also revealed the 1,3- and 1,5-diaxial relationship for the sugars of the pyranosyl rings, thus greatly facilitating the mapping of these spin systems. Information from COSY, TOCSY, and NOESY gave the complete assignment of all protons of the compound. On the basis of the assigned protons, the $^{13}$C resonances of each sugar unit were identified by HSQC and further confirmed by HMBC. Interpretation of the COSY and TOCSY spectra revealed the presence of 5 glycosyl residues. Measurement of the magnitude of homonuclear $^1$H-$^1$H scalar couplings provided geometric information that allowed the glycosyl configuration corresponding to each isolated spin system to be identified. The magnitude of homonuclear $^1$H-$^1$H scalar couplings combined with the strong NOEs between H-1 and H-3, H-1 and H-5 in all the five glycosyl residues as well as the $^{13}$C NMR data identified all the sugar components to be β-glucose.

The linkages between the glycosyl residues were assigned by several complementary approaches. The initial assignment of the glycosyl linkages was based on NOE contacts between H-1 resonances and resonances of the aglyconic residues. The NOE contact between H-1 of G-1 (δ 4.77 ppm) and H-2 of G-2 (δ 3.61 ppm) was diagnostic for the 1→2 linkage between these two glycosyl residues. Similarly, the NOE contacts between H-1 of G-5 (δ 4.29 ppm) and both H-6 (δ 3.63, 4.24 ppm) of G-2 indicated the 1→6 connection. At the same time, a strong NOE was also observed between the H-1 of G-2 (δ 4.43 ppm) and H-24 of the aglycone, mogrol (δ 3.40 ppm). Thus, the two terminal glucose residues (G-1 and 0-5) were linked through a 2,6-branched glucose (G-2) to C-24 of mogrol. The NOE contact between H-1 of G-3 (δ 4.42 ppm) and H-4 of G-4 (δ 3.55 ppm) indicated that the two remaining glycosyl residues were linked via a 1→4 linkage and the disaccharide was connected to C-4 of the aglycone based on a strong NOE contact between H-1 of G-4 (δ 4.31 ppm) and H-3 of the aglycone (δ 3.47 ppm). However, due to the highly overlapping nature of the proton NMR of the glycosyl residues, to ensure accuracy, NOE should not be used as the sole source of data for the inter-sugar linkage. Therefore, the sugar linkage was further confirmed by HMBC. The linkage of the sugar units at C-24 was established from the following HMBC correlations: H-1 of G-1 (δ 4.77 ppm) and C-2 of G-2 (δ 81.3 ppm); H-1 of G-5 (δ 4.29 ppm) and C-6 of G-2 (δ 70.2 ppm). The attachment of the trisaccharide moiety to C-24 of the aglycone was confirmed by the long-range coupling between H-1 of G-2 (δ 4.43 ppm and C-24 of the mogrol (δ 93.5 ppm). The crosspeak between H-1 of G-3 (δ 4.42 ppm) and C-4 of G-4 (δ 80.9 ppm) confirmed the 1→4 linkage between the remaining two glucose units. The attachment site of the disaccharide was further confirmed from the long-range coupling between H-1 of G-4 (δ 4.31 ppm) to that of C-3 of mogrol (δ 88.3 ppm).

The fragmentation patterns observed by ESI-MS/MS confirm the results of the above sugar sequence analysis.

MS/MS analysis of the deprotonated molecular ion [M−H]$^-$ (m/z 1285.6) gave a series of daughter ions (m/z 1223.9 [(M−H)−162]$^-$, m/z 961.8 [(M−H)−2×162]$^-$, m/z 799.7 [(M−H)−3×162]$^-$, m/z 637.6 [(M−H)−4×162]$^-$, and m/z 475.5 [mogrol, (M−H)−5×162]$^-$ by subsequent loss of the terminal glucose residues.

The formula below shows the key NOE contacts and HMBC long-ranged couplings for iso-mogroside V (1).

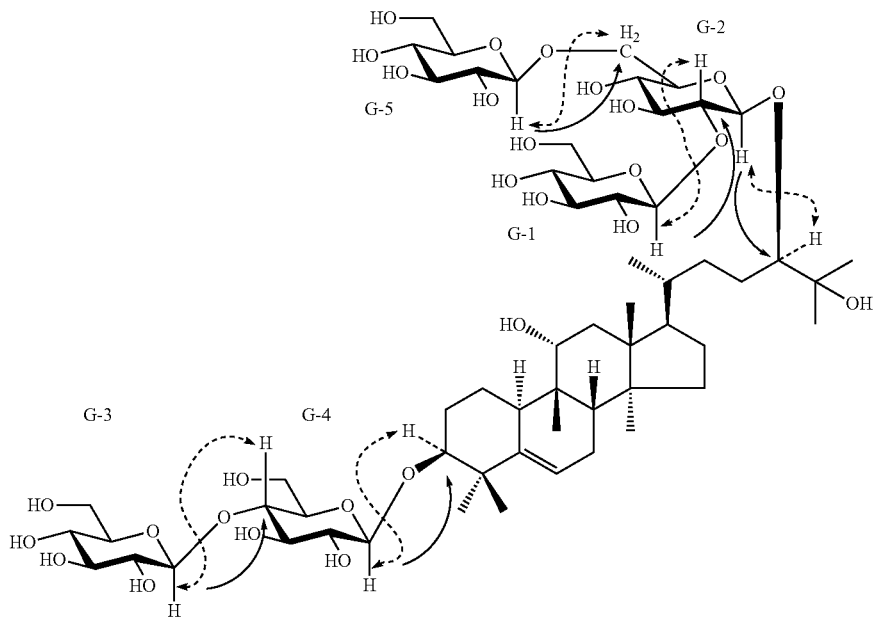

All the glycosyl residues were in the pyranose form as determined from their $^{13}$C NMR data. The β-anomeric configurations were evident from their $^3J_{H1,H2}$ (7-8 Hz) coupling constants as well as from NOE information.

As the compounds (iso-mogroside V, mogroside V) are derived from a natural botanical source, the glucose residues all have D-configuration.

Thus, the structure of iso-mogroside V (1) was established as 3-[(4-O-β-D-glucopyranosyl-β-D-glucopyranosyl)oxy]-mogrol-24-O-β-D-glucopyranosyl-(1→2)-O-[β-D-glucopyranosyl-(1→6)]-β-D-glucopyranoside.

As comparison, the detailed NMR analyses were also carried out on the major sweet component, mogroside V (2). The completed NMR assignment was achieved by a combination of COSY, TOCSY, NOESY, HSQC and HMBC (see summary of the $^1$H and $^{13}$C NMR data from these methods in the respective tables above).

Figure 2:
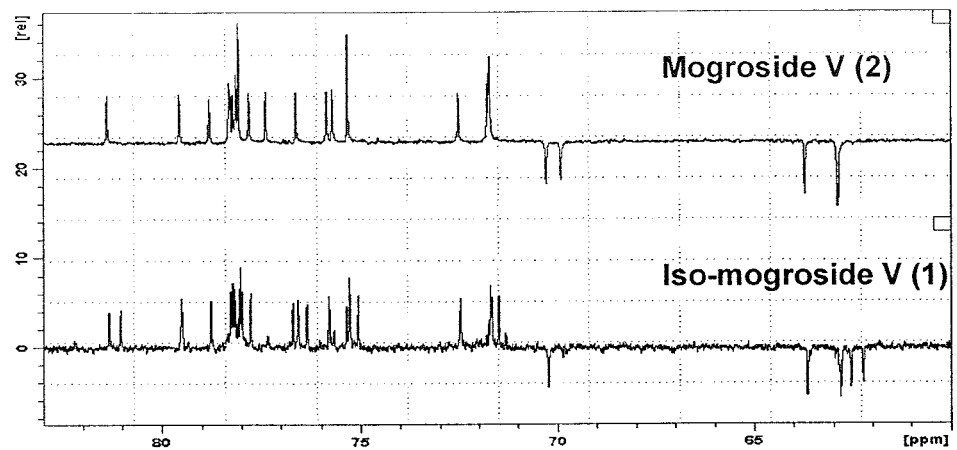
FIG. 2 is a DEPT spectra of Iso-mogroside V.
Figure 3:
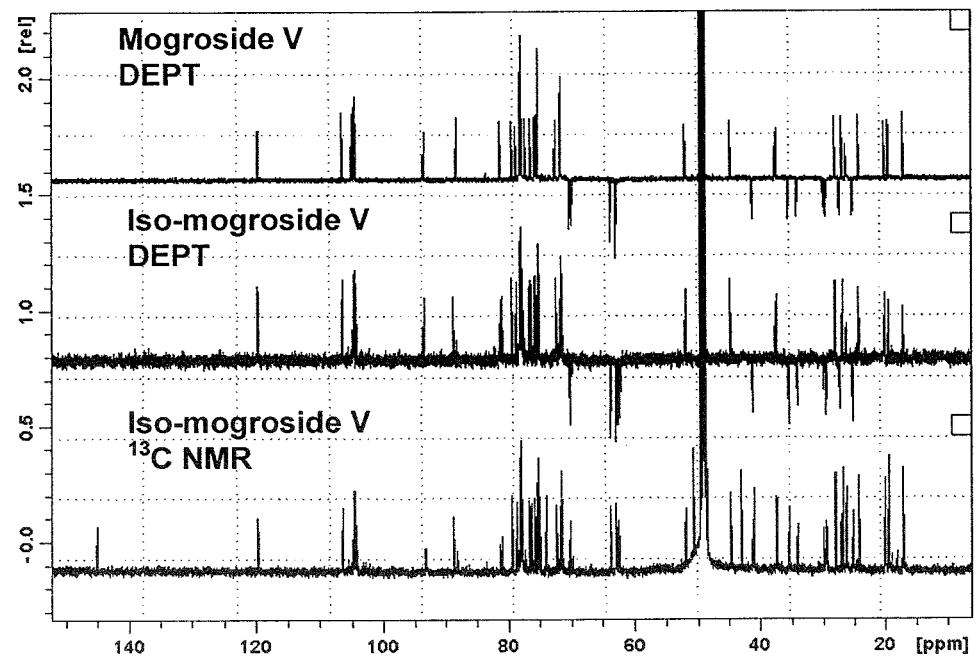
FIG. 3 is a DEPT spectra of Mogroside V.

A direct comparison of the DEPT (Distortionless Enhancement by Polarization Transfer) spectra of iso-mogroside V (1) and mogroside V (2) clearly showed the difference between the two isomers, see results in FIG. 2 and FIG. 3.

FIG. 3 shows the complete spectrum from 6 to 150 ppm, and FIG. 2 shows an enlargement of the sugar part from 60 to 85 ppm. The x-axis of both figures gives the δ ppm, the y axis of both figures gives the relative intensity.

Looking at the enlargement of the field, the free, non-glycosylated C-6 of the glucose residues appeared in the region of δ 60-64 ppm in the $^{13}$C NMR spectra as expected.

For mogroside V (2), two C-6 of the glucose residues were found in the downfield region at around δ 70 ppm indicating that two of the five glucose residues were glycosylated at C-6 position. However, for iso-mogroside V (1), only one 1,6-glycosylated C-6 of a glucose residue was found (compare the figure at 70 ppm).

Furthermore, another $^{13}$C resonance was found at around δ 81 ppm indicating that one of the terminal glucose residues was, instead of the 1,6-glycosidic bond as in mogroside V, attached elsewhere to the ring (the linkage was identified as 1,4-glycosidic by further analysis employing 2D NMR).

Accordingly, iso-mogroside V was identified as an isomer of mogroside V wherein the difference of the two isomers is the linkage between the G-3 and G-4 glucose residues (iso-mogroside V: 1,4-β-glycosidic, mogroside V: 1,6-β-glycosidic). Both compounds displayed almost identical HPLC retention times and identical MS/MS fragmentation patterns.

The invention claimed is:

1. A consumable composition comprising 3-[(4-O-β-D-glucopyranosyl-β-D-glucopyranosyl)oxy]-mogrol-24-O-β-D-glucopyranosyl-(1→2)-O-[β-D-glucopyranosyl-(1→6)]-β-D-glucopyranoside (iso-mogroside V), wherein the iso-mogroside V is present in a concentration of 10-200 ppm, and wherein the composition further comprises at least one excipient.

2. The composition of claim 1 wherein the iso-mogroside V is isosweet to 0.5% sucrose.

3. The composition of claim 1 wherein the composition further comprises at least one sweetener selected from the group consisting of: sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, mogroside IV, siamenoside I, mogroside V, and trilobatin.

4. The composition of claim 1 wherein the composition is a water-based consumable selected from: beverage, water, aqueous beverage, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacoa, tea-based drink, coffee-based drinks, cacao-based drink, syrup, frozen fruit, frozen fruit juice, water-based ice, fruit ice, sorbet, dressing, salad dressing, sauce, soup, and beverage botanical materials, or instant powder for reconstitution.

5. The composition of claim 1 wherein the composition is a solid dry consumable selected from: cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, botanical materials (whole or ground), and instant powders for reconstitution.

6. The composition of claim 1 wherein the composition is a consumable selected from: a dairy product, a dairy-derived product and a dairy-alternative product selected from: milk, fluid milk, cultured milk product, cultured and noncultured dairy-based drink, cultured milk product cultured with *lactobacillus*, yoghurt, yoghurt-based beverage, smoothy, lassi, milk shake, acidified milk, acidified milk beverage, butter milk, kefir, milk-based beverages, milk/juice blend, fermented milk beverage, ice cream, dessert, sour cream, dip, salad dressing, cottage cheese, frozen yoghurt, soy milk, rice milk, soy drink, and rice milk drink.

7. A method of providing a sweetened consumable, the method comprising the step of: admixing 3-[(4-O-β-D-glucopyranosyl-β-D-glucopyranosyl)oxy]-mogrol-24-O-β-D-glucopyranosyl-(1→2)-O-[β-D-glucopyranosyl-(1→6)]-β-D glucopyranoside (iso-mogroside V) with a consumable to provide a resultant total concentration of iso-mogroside V of 10-200 ppm in the consumable, and wherein the consumable comprises at least one excipient.

8. The method according to claim 7 wherein the consumable further comprises a sweetener.

9. The method according to claim 8 wherein the sweetener is selected from the group consisting of: sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, mogroside IV, siamenoside I, mogroside V, and trilobatin.

10. The method according to claim 7 wherein the consumable is a water-based consumable.

11. The method according to claim 7 wherein the consumable is a solid dry consumable.

12. The method according to claim 7 wherein the consumable is a dairy product, a dairy-derived product or a dairy-alternative product.

13. An additive which when combined with a consumable composition when the additive is present in a concentration of 10-200 ppm, the additive comprising 3-[(4-O-β-D-glucopyranosyl-β-D-glucopyranosyl)oxy]-mogrol-24-O-β-D-glucopyranosyl-(1→2)-O-[β-D-glucopyranosyl-(1→6)]-β-D-glucopyranoside (iso-mogroside V), and wherein the consumable composition further comprises at least one excipient.

14. The additive of claim 13 which at a concentration of 10 ppm is isosweet to 0.5% sucrose.

15. The additive of claim 13 wherein two glucose molecules are connected through a (1-4) glycosidic linkage instead of a (1-6) linkage.

16. The additive of claim 13 which further comprises at least one sweetener selected from the group consisting of: sucrose, fructose, glucose, high fructose corn syrup, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, rebaudioside A, stevioside, mogroside IV, siamenoside I, mogroside V, and trilobatin.

17. A consumable comprising the additive of claim 13.

18. The consumable of claim 17, wherein the consumable is a water-based consumable selected from: beverage, water, aqueous beverage, enhanced/slightly sweetened water drink, mineral water, carbonated beverage, non-carbonated beverage, carbonated water, still water, soft drink, non-alcoholic drink, alcoholic drink, beer, wine, liquor, fruit drink, juice, fruit juice, vegetable juice, broth drink, coffee, tea, black tea, green tea, oolong tea, herbal tea, cacoa, tea-based drink, coffee-based drinks, cacao-based drink, syrup, frozen fruit, frozen fruit juice, water-based ice, fruit ice, sorbet, dressing, salad dressing, sauce, soup, and beverage botanical materials, or instant powder for reconstitution.

19. The consumable of claim 17, wherein the consumable is selected from: cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, botanical materials (whole or ground), and instant powders for reconstitution.

20. The consumable of claim 17 wherein the consumable is selected from: milk, fluid milk, cultured milk product, cultured and noncultured dairy-based drink, cultured milk product cultured with *lactobacillus*, yoghurt, yoghurt-based beverage, smoothy, lassi, milk shake, acidified milk, acidified milk beverage, butter milk, kefir, milk-based beverages, milk/juice blend, fermented milk beverage, ice cream, dessert, sour cream, dip, salad dressing, cottage cheese, frozen yoghurt, soy milk, rice milk, soy drink, and rice milk drink.

21. The composition of claim 1, wherein the iso-mogroside V is isolated or purified.

22. The method of claim 7, wherein the iso-mogroside V is isolated or purified.

23. The additive of claim 13, wherein the iso-mogroside V is isolated or purified.

* * * * *

UNITED STATES PATENT AND TRADEMARK OFFICE
CERTIFICATE OF CORRECTION

PATENT NO. : 11,154,071 B2
APPLICATION NO. : 14/806239
DATED : October 26, 2021
INVENTOR(S) : Zhonghua Jia et al.

It is certified that error appears in the above-identified patent and that said Letters Patent is hereby corrected as shown below:

On the Title Page

Item (54) and in the Specification, Column 1, Line 1, should read "NOVEL SWEETENER ISO-MOGROSIDE V".

Item (71) should read, in part, "Givaudan SA".

Signed and Sealed this
First Day of March, 2022

Drew Hirshfeld
*Performing the Functions and Duties of the*
*Under Secretary of Commerce for Intellectual Property and*
*Director of the United States Patent and Trademark Office*